United States Patent
Malek Tabrizi et al.

(10) Patent No.: US 12,138,201 B2
(45) Date of Patent: *Nov. 12, 2024

(54) METHODS FOR LENTICULAR LASER INCISION

(71) Applicant: AMO Development, LLC, Irvine, CA (US)

(72) Inventors: Alireza Malek Tabrizi, Fremont, CA (US); Hong Fu, Pleasanton, CA (US); James E. Hill, Santa Ana, CA (US); Mohammad Saidur Rahaman, Santa Clara, CA (US); Zenon Witowski, Pleasanton, CA (US)

(73) Assignee: AMO Development, LLC, Irvine, CA (US)

( * ) Notice: Subject to any disclaimer, the term of this patent is extended or adjusted under 35 U.S.C. 154(b) by 87 days.

This patent is subject to a terminal disclaimer.

(21) Appl. No.: 17/651,242

(22) Filed: Feb. 15, 2022

(65) Prior Publication Data
US 2022/0168144 A1    Jun. 2, 2022

Related U.S. Application Data

(63) Continuation of application No. 15/630,629, filed on Jun. 22, 2017, now Pat. No. 11,253,398.
(Continued)

(51) Int. Cl.
*A61F 9/008* (2006.01)
*A61B 18/20* (2006.01)
*A61B 18/00* (2006.01)

(52) U.S. Cl.
CPC ............ *A61F 9/0084* (2013.01); *A61B 18/20* (2013.01); *A61F 9/00827* (2013.01);
(Continued)

(58) Field of Classification Search
CPC .. A61F 2009/00872; A61F 2009/00897; A61F 9/00827; A61F 9/0084
See application file for complete search history.

(56) References Cited

U.S. PATENT DOCUMENTS

| 4,665,913 A | 5/1987 | L'Esperance, Jr. |
| 4,669,466 A | 6/1987 | L'Esperance |

(Continued)

FOREIGN PATENT DOCUMENTS

| WO | 2009158723 A2 | 12/2009 |
| WO | 2014140182 A1 | 9/2014 |
| WO | 2016049442 A1 | 3/2016 |

OTHER PUBLICATIONS

International Preliminary Report on Patentability for Application No. PCT/US2017/038836, mailed on Dec. 25, 2018, 9 pages.
(Continued)

*Primary Examiner* — Scott Luan

(57) ABSTRACT

Embodiments generally relate to ophthalmic laser procedures and, more particularly, to systems and methods for lenticular laser incision. In an embodiment, an ophthalmic surgical laser system comprises a laser delivery system for delivering a pulsed laser beam to a target in a subject's eye, an XY-scan device to deflect the pulsed laser beam, a Z-scan device to modify a depth of a focus of the pulsed laser beam, and a controller configured to form a top lenticular incision and a bottom lenticular incision of a lens in a corneal stroma.

11 Claims, 16 Drawing Sheets

Related U.S. Application Data

(60) Provisional application No. 62/353,500, filed on Jun. 22, 2016.

(52) U.S. Cl.
CPC ........... *A61B 2018/00601* (2013.01); *A61F 2009/00872* (2013.01); *A61F 2009/00897* (2013.01)

(56) References Cited

U.S. PATENT DOCUMENTS

| | | |
|---|---|---|
| 4,732,148 A | 3/1988 | L'Esperance, Jr. |
| 4,764,930 A | 8/1988 | Bille et al. |
| 4,770,172 A | 9/1988 | L'Esperance, Jr. |
| 4,773,414 A | 9/1988 | L'Esperance, Jr. |
| 5,108,388 A | 4/1992 | Trokel et al. |
| 5,163,934 A | 11/1992 | Munnerlyn |
| 5,207,668 A | 5/1993 | L'Esperance, Jr. |
| 5,219,343 A | 6/1993 | L'Esperance, Jr. |
| 5,646,791 A | 7/1997 | Glockler |
| 5,993,438 A | 11/1999 | Juhasz et al. |
| 6,315,413 B1 | 11/2001 | Shimmick et al. |
| 8,260,024 B2 | 9/2012 | Farrer et al. |
| 8,394,084 B2 | 3/2013 | Blumenkranz et al. |
| 8,403,921 B2 | 3/2013 | Blumenkranz et al. |
| 8,690,862 B2 | 4/2014 | Palanker et al. |
| 8,709,001 B2 | 4/2014 | Blumenkranz et al. |
| 9,521,949 B2 | 12/2016 | Bor et al. |
| 2004/0243112 A1* | 12/2004 | Bendett ............... A61F 9/00827 606/5 |
| 2008/0077121 A1* | 3/2008 | Rathjen ............... A61F 9/00827 606/5 |
| 2011/0172649 A1 | 7/2011 | Schuele et al. |
| 2012/0078240 A1* | 3/2012 | Spooner .............. A61F 9/00827 606/17 |
| 2012/0310224 A1* | 12/2012 | Miyagi ............... A61F 9/00827 606/5 |
| 2013/0131653 A1 | 5/2013 | Huang |
| 2014/0128855 A1 | 5/2014 | Wottke et al. |
| 2014/0128857 A1 | 5/2014 | Wottke et al. |
| 2015/0018674 A1 | 1/2015 | Scott et al. |

OTHER PUBLICATIONS

International Search Report and Written Opinion for Application No. PCT/US2017/038836, mailed on Sep. 27, 2017, 17 pages.

Menzel-Severing J., et al., "Evaluation of a 345 nm Femtosecond Laser for Corneal Surgery With Respect to Intraocular Radiation Hazard," Intraocular Hazard of 345 nm Femtosecond Laser, PloS One, Sep. 11, 2015, pp. 1-16, DOI:10.1371/journal.pone.0137638.

* cited by examiner

METHODS FOR LENTICULAR LASER INCISION

RELATED APPLICATIONS

This application is a continuation of U.S. patent application Ser. No. 15/630,629, filed Jun. 22, 2017, allowed, which claims priority to, and the benefit of, under 35 U.S.C. § 119(e) of U.S. Provisional Appl. No. 62/353,500, filed Jun. 22, 2016. The above-referenced applications are herein incorporated by reference in their entireties.

FIELD

Embodiments of this invention relate generally to laser-assisted ophthalmic procedures, and more particularly, to systems and methods for lenticular incisions in the cornea.

BACKGROUND

Vision impairments such as myopia (near-sightedness), hyperopia and astigmatism can be corrected using eyeglasses or contact lenses. Alternatively, the cornea of the eye can be reshaped surgically to provide the needed optical correction. Eye surgery has become commonplace with some patients pursuing it as an elective procedure to avoid using contact lenses or glasses to correct refractive problems, and others pursuing it to correct adverse conditions such as cataracts. And, with recent developments in laser technology, laser surgery is becoming the technique of choice for ophthalmic procedures. The reason eye surgeons prefer a surgical laser beam over manual tools like microkeratomes and forceps is that the laser beam can be focused precisely on extremely small amounts of ocular tissue, thereby enhancing accuracy and reliability of the procedure. These in turn enable better wound healing and recovery following surgery.

Hyperopia (far-sightedness) is a visual impairment where light entering the eye does not focus at the retina to produce a sharp image as desired, but rather focuses at a location behind the retina such that a patient sees a blurred disc. The basic principle to treating hyperopia is to add positive focusing power to the cornea. For instance, a hyperopic eye can be treated by placing a convex lens in front of the eye to add a positive focusing power to the eye. After correction, light passing through the convex lens and into the eye focuses at the retina to form a sharp image.

Different laser eye surgical systems use different types of laser beams for the various procedures and indications. These include, for instance, ultraviolet lasers, infrared lasers, and near-infrared, ultra-short pulsed lasers. Ultra-short pulsed lasers emit radiation with pulse durations as short as 10 femtoseconds and as long as 3 nanoseconds, and a wavelength between 300 nm and 3000 nm. Examples of laser systems that provide ultra-short pulsed laser beams include the Abbott Medical Optics iFS Advanced Femtosecond Laser, the IntraLase FS Laser, and the OptiMedica Catalys Precision Laser System.

Prior surgical approaches for reshaping the cornea include laser assisted in situ keratomileusis (hereinafter "LASIK"), photorefractive keratectomy (hereinafter "PRK") and Small Incision Lens Extraction (hereinafter "SMILE").

In the LASIK procedure, an ultra-short pulsed laser is used to cut a corneal flap to expose the corneal stroma for photoablation with ultraviolet beams from an excimer laser. Photoablation of the corneal stroma reshapes the cornea and corrects the refractive condition such as myopia, hyperopia, astigmatism, and the like.

It is known that if a part of the cornea is removed, the pressure exerted on the cornea by the aqueous humor in the anterior chamber of the eye will act to close the void created in the cornea, resulting in a reshaped cornea. By properly selecting the size, shape and location of a corneal void, one can obtain the desired shape, and hence, the desired optical properties of the cornea.

In traditional laser surgery treatments, such as LASIK and PRK that correct hyperopia, positive focusing power is added to the cornea by steepening the curvature of the cornea, by for example, removing a ring-shaped stroma material from the cornea. As described earlier, in a LASIK procedure, a flap is first created, and then lifted so the ring-shaped stroma material can be removed or ablated away by an excimer laser. The center of the cornea is not removed while more outward portions of the cornea are removed. The flap is then put back into place. The cornea thus steepens due to the void created in the cornea. Common patterns that steepen the cornea include ring, tunnel, and toric shapes. LASIK can typically correct hyperopia for up to 5D (diopter). In a PRK procedure, no flap is created in the cornea. Instead, an excimer laser is used to first remove the epithelium layer, and then, the ring-shaped stroma material. Typically, the epithelium layer grows back a few days after the PRK procedure.

More recently, surgeons have started using another surgical technique called small incision lenticule extraction (SMILE) for refractive correction. The SMILE procedure is different from LASIK and PRK. Instead of ablating corneal tissue with an excimer laser, the SMILE technique involves tissue removal with two femtosecond laser incisions that intersect to create a lenticule, which is then extracted. Lenticular extractions can be performed either with or without the creation of a corneal flap. With the flapless procedure, a refractive lenticule is created in the intact portion of the anterior cornea and removed through a small incision.

In the SMILE procedure illustrated in FIG. 10, a femtosecond laser 110 is used to make a side cut 120, an upper surface cut 130, and a lower surface cut 140 that forms a cut lens 150. An instrument like a tweezer, for example, is then used to extract the cut lens beneath the anterior surface of the cornea 160 through the side cut 120.

While, SMILE has been applied to treat myopia by cutting and extracting a convex lens-shaped stroma material with a femtosecond laser, the technique has not been applied in treating hyperopia.

Further, as shown in FIG. 1, conventional femtosecond laser surgery systems generate a curved dissection surface to make a lenticular incision by scanning a laser focus on the intended dissection surface through a XY-scanning device and a Z-scanning device. This method does not use the more advantageous "fast-scan-slow-sweep" scanning scheme with femtosecond lasers having high repetition rate ("rep rate"), for e.g., in the MHz range. Using the "fast-scan-slow-sweep" scanning scheme for a lenticular incision, however, will generate vertical "steps" and will require many vertical side cuts, resulting in a lenticular dissection surface that is not smooth.

Therefore, there is a need for improved systems and methods to generate corneal lenticular incisions for high repetition rate femtosecond lasers to correct hyperopia.

SUMMARY

Hence, to obviate one or more problems due to limitations and disadvantages of the related art, this disclosure provides embodiments including an ophthalmic surgical laser system comprising a laser delivery system for delivering a pulsed laser beam to a target in a subject's eye, an XY-scan device to deflect the pulsed laser beam, a Z-scan device to modify a depth of a focus of the pulsed laser beam, and a controller configured to form a top lenticular incision and a bottom lenticular incision of a lens on the subject's eye. The XY-scan device deflects the pulsed laser beam to form a scan line. The scan line is tangential to the parallels of latitude of the lens. The scan line is then moved along the meridians of longitude of the lens. The top lenticular incision is moved over the top surface of the lens through the apex of the top surface of the lens, and the bottom lenticular incision is moved over the bottom surface of the lens through the apex of bottom surface of the lens.

Other embodiments disclose an ophthalmic surgical laser system comprising a laser delivery system for delivering a pulsed laser beam to a target in a subject's eye, an XY-scan device to deflect the pulsed laser beam, a Z-scan device to modify a depth of a focus of the pulsed laser beam, and a controller configured to form a top concave lenticular incision and a bottom concave lenticular incision of a lens on the subject's eye.

Methods and systems here include directing an ophthalmic surgical femtosecond laser beam into an intrastromal corneal layer of a patient, pre-compensating dispersion of the laser beam path, focusing the laser beam into a focal spot to disrupt cells in the intrastromal corneal layer, moving the laser beam to create a pattern of spaced focal spots inside the intrastromal corneal layer, incising a lens with the spaced focal spots in the intrastromal corneal layer of the patient. Alternatively or additionally, a wavelength of the laser is between 300 nm and 1100 nm. Alternatively or additionally, a wavelength of the laser is between 1020 nm and 1065 nm. Alternatively or additionally, a spot size is between 0.3 µm and 1.5 µm in diameter. Alternatively or additionally, a spot size is between 0.9 µm and 1.11 µm in diameter. Alternatively or additionally, the spot spacing is between 0.2 µm and 2 µm from center to center of the spots. Alternatively or additionally, the spot spacing is less than 1 µm from center to center of the spots. Alternatively or additionally, the spots in the pattern overlap. Alternatively or additionally, a frequency of the laser is between 1 and 20 MHz. Alternatively or additionally, a frequency of the laser is 10 MHz. Alternatively or additionally, a pulse width of the laser is between 50 fs and 200 fs. Alternatively or additionally, a pulse width of the laser is between 100 fs and 200 fs. Alternatively or additionally, an energy for one spot is between 20 nJ and 200 nJ. Alternatively or additionally, an energy for one spot is between 70 nJ and 130 nJ. In some embodiments, scanning the laser beam to produce a scan line, wherein the scanning is between 2,000 Hz to 20,000 Hz.

This summary and the following detailed description are merely exemplary, illustrative, and explanatory, and are not intended to limit, but to provide further explanation of the embodiments as claimed. Additional features and advantages of the embodiments will be set forth in the descriptions that follow, and in part will be apparent from the description, or may be learned by practice of the embodiments. The objectives and other advantages of the embodiments will be realized and attained by the structure particularly pointed out in the written description, claims and the appended drawings.

BRIEF DESCRIPTION OF THE DRAWINGS

The novel features of the embodiments are set forth with particularity in the appended claims. A better understanding of the features and advantages will be facilitated by referring to the following detailed description that sets forth illustrative embodiments using principles of the embodiments, as well as to the accompanying drawings, in which like numerals refer to like parts throughout the different views Like parts, however, do not always have like reference numerals. Further, the drawings are not drawn to scale, and emphasis has instead been placed on illustrating the principles of the embodiments. All illustrations are intended to convey concepts, where relative sizes, shapes, and other detailed attributes may be illustrated schematically rather than depicted literally or precisely.

DETAILED DESCRIPTION OF THE PREFERRED EMBODIMENTS

Embodiments of this invention are generally directed to systems and methods for laser-assisted ophthalmic procedures, and more particularly, to systems and methods for lenticular laser incisions.

Figure 1:
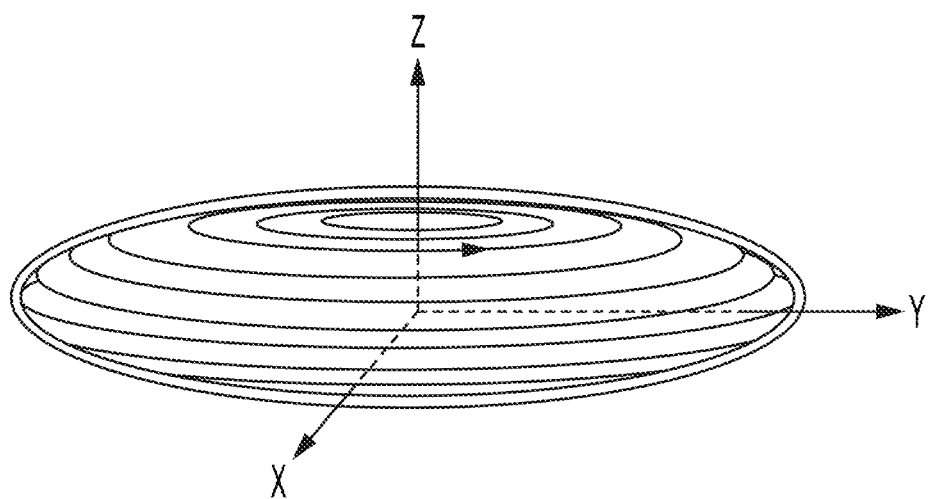
FIG. 1 illustrates a conventional lenticular cut via scanning a single focus spot.
Figure 2:
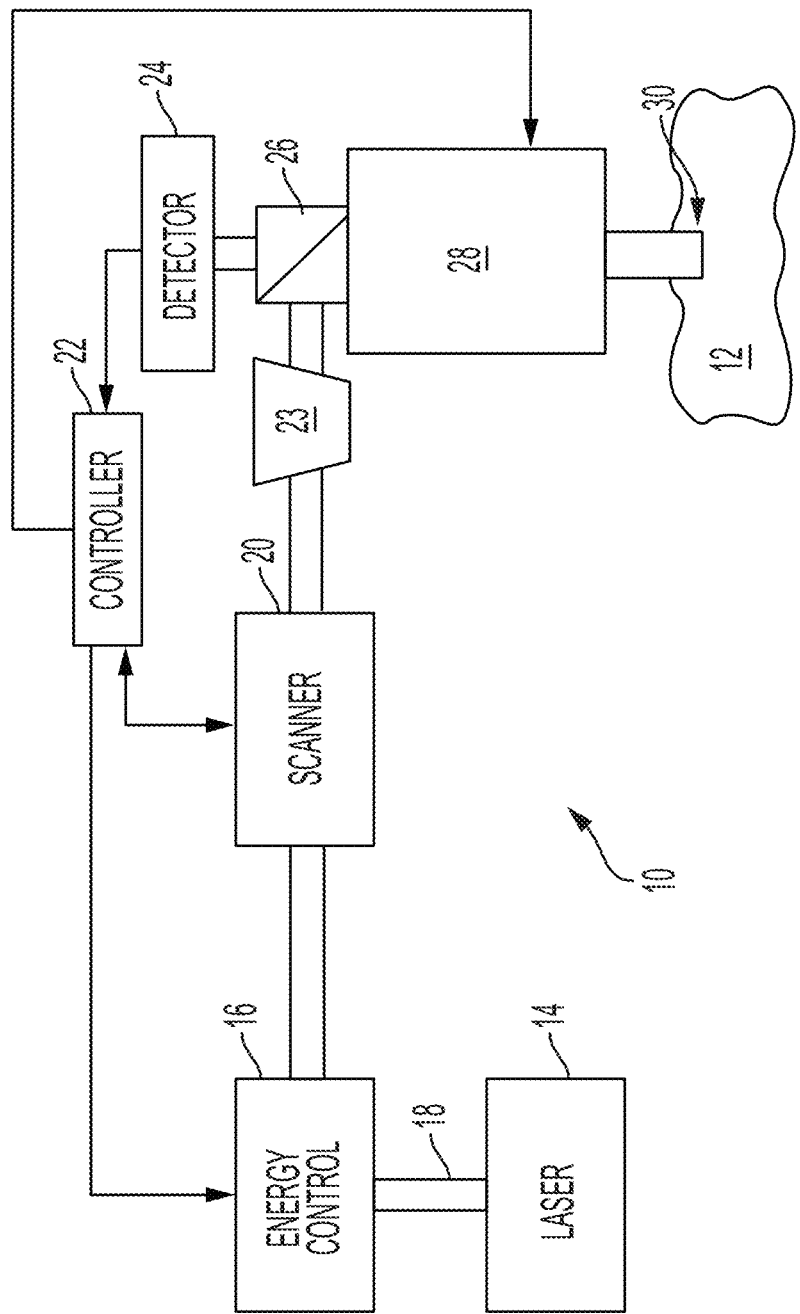
FIG. 2 is a simplified diagram of a surgical ophthalmic laser system according to some embodiments.

Referring to the drawings, FIG. 2 shows a system 10 for making an incision in a material 12. The system 10 includes, but is not limited to, a laser 14 capable of generating a pulsed laser beam 18, an energy control module 16 for varying the pulse energy of the pulsed laser beam 18, a Z-scanner 20 for modifying the depth of the pulse laser beam 18, a controller 22, a prism 23 (e.g., a Dove or Pechan prism, or the like), and an XY-scanner 28 for deflecting or directing the pulsed laser beam 18 from the laser 14 on or within the material 12. The controller 22, such as a processor operating suitable control software, is operatively coupled with the Z-scanner 20, the XY-scanner 28, and the energy control unit 16 to direct a scan line 30 of the pulsed laser beam along a scan pattern on or in the material 12. In this embodiment, the system 10 further includes a beam splitter 26 and a detector 24 coupled to the controller 22 for a feedback control mechanism (not shown) of the pulsed laser beam 18. Other feedback methods may also be used, including but not necessarily limited to position encoder on the scanner 20, or the like. In an embodiment, the pattern of pulses may be summarized in machine readable data of tangible storage media in the form of a treatment table. The treatment table may be adjusted according to feedback input into the controller 22 from an automated image analysis system in response to feedback data provided from an ablation monitoring system feedback system (not shown). Optionally, the feedback may be manually entered into the controller 22 by a system operator. The feedback may also be provided by integrating a wavefront measurement system (not shown) with the laser surgery system 10. The controller 22 may continue and/or terminate a sculpting or incision in response to the feedback, and may also modify the planned sculpting or incision based at least in part on the feedback. Measurement and imaging systems are further described in U.S. Pat. Nos. 6,315,413 and 8,260,024, the complete disclosures of which are incorporated herein by reference.

In an embodiment, the system 10 uses a pair of scanning mirrors or other optics (not shown) to angularly deflect and scan the pulsed laser beam 18. For example, scanning mirrors driven by galvanometers may be employed where each of the mirrors scans the pulsed laser beam 18 along one of two orthogonal axes. A focusing objective (not shown), whether one lens or several lenses, images the pulsed laser beam 18 onto a focal plane of the system 10. The focal point of the pulsed laser beam 18 may thus be scanned in two dimensions (e.g., the x-axis and the y-axis) within the focal plane of the system 10. Scanning along the third dimension, i.e., moving the focal plane along an optical axis (e.g., the z-axis), may be achieved by moving the focusing objective, or one or more lenses within the focusing objective, along the optical axis.

Laser 14 may comprise a femtosecond laser capable of providing pulsed laser beams, which may be used in optical procedures, such as localized photodisruption (e.g., laser induced optical breakdown). Localized photodisruptions can be placed at or below the surface of the material to produce high-precision material processing. For example, a micro-optics scanning system may be used to scan the pulsed laser beam to produce an incision in the material, create a flap of the material, create a pocket within the material, form removable structures of the material, and the like. The term "scan" or "scanning" refers to the movement of the focal point of the pulsed laser beam along a desired path or in a desired pattern.

In other embodiments, the laser 14 may comprise a laser source configured to deliver an ultraviolet laser beam comprising a plurality of ultraviolet laser pulses capable of photodecomposing one or more intraocular targets within the eye.

Although the laser system 10 may be used to photoalter a variety of materials (e.g., organic, inorganic, or a combination thereof), the laser system 10 is suitable for ophthalmic applications in some embodiments. In these cases, the focusing optics direct the pulsed laser beam 18 toward an eye (for example, onto or into a cornea) for plasma mediated (for example, non-UV) photoablation of superficial tissue, or into the stroma of the cornea for intrastromal photodisruption of tissue. In these embodiments, the surgical laser system 10 may also include a lens to change the shape (for example, flatten or curve) of the cornea prior to scanning the pulsed laser beam 18 toward the eye.

The laser system 10 is capable of generating the pulsed laser beam 18 with physical characteristics similar to those of the laser beams generated by a laser system disclosed in U.S. Pat. Nos. 4,764,930, 5,993,438, and U.S. patent application Ser. No. 12/987,069, filed Jan. 7, 2011, which are incorporated herein by reference.

Figure 3:
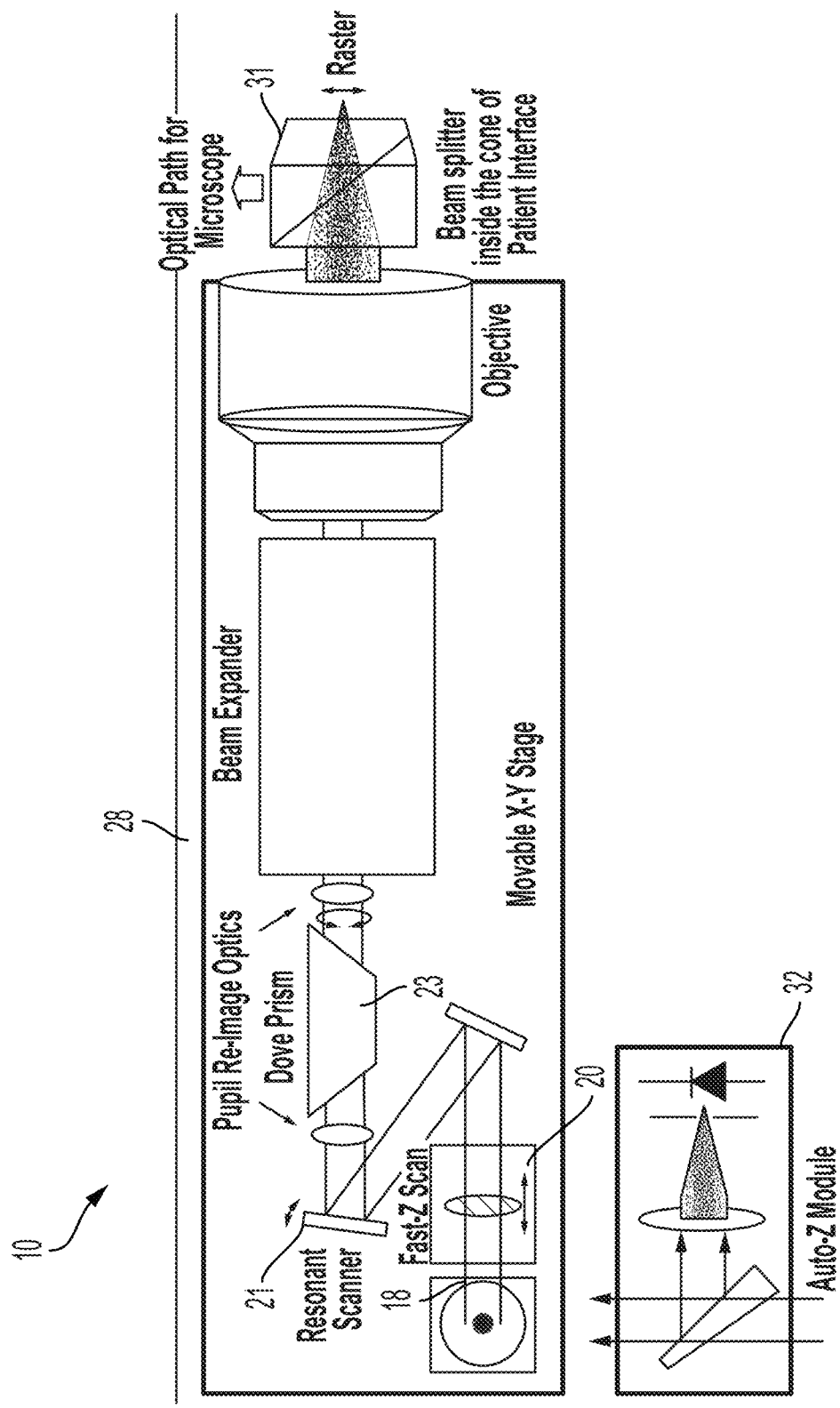
FIG. 3 is another simplified diagram of a surgical ophthalmic laser system according to some embodiments.

FIG. 3 shows another exemplary diagram of the laser system 10. FIG. 3 shows a moveable XY-scanner (or XY-stage) 28 of a miniaturized femtosecond laser system. In this embodiment, the system 10 uses a femtosecond oscillator, or a fiber oscillator-based low energy laser. This allows the laser to be made much smaller. The laser-tissue interaction is in the low-density-plasma mode. An exemplary set of laser parameters for such lasers include pulse energy in the 50-100 nJ range and pulse repetitive rates (or "rep rates") in the 5-20 MHz range. A fast-Z scanner 20 and a resonant scanner 21 direct the laser beam 18 to the prism 23. When used in an ophthalmic procedure, the system 10 also includes a patient interface 31 design that has a fixed cone nose and a portion that engages with the patient's eye. A beam splitter is placed inside the cone of the patient interface to allow the whole eye to be imaged via visualization optics. In one embodiment, the system 10 uses: optics with a 0.6 numerical aperture (NA) which would produce 1.1 μm Full Width at Half Maximum (FWHM) focus spot size; and a resonant scanner 21 that produces 1-2 mm scan line with the XY-scanner scanning the resonant scan line to a 10 mm field. The prism 23 rotates the resonant scan line in any direction on the XY plane. The fast-Z scanner 20 sets the incision depth and produces a side cut. The system 10 may also include an auto-Z module 32 to provide depth reference. The miniaturized femtosecond laser system 10 may be a desktop system so that the patient sits upright while being under treatment. This eliminates the need of certain opto-mechanical arm mechanism(s), and greatly reduces the complexity, size, and weight of the laser system. Alternatively, the miniaturized laser system may be designed as a conventional femtosecond laser system, where the patient is treated while lying down.

Figure 4:
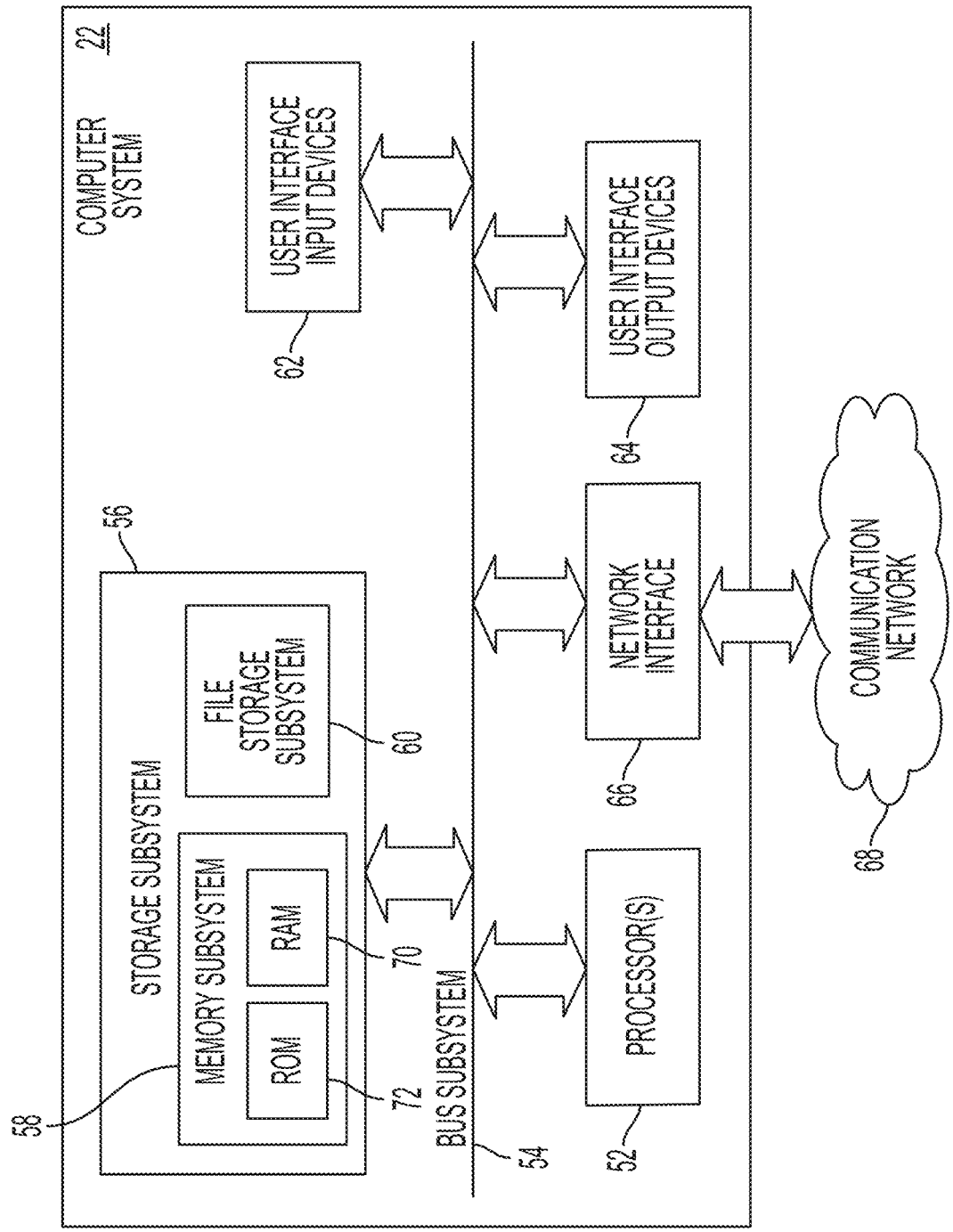
FIG. 4 is a simplified diagram of a controller of a surgical ophthalmic laser system according to some embodiments.

FIG. 4 illustrates a simplified block diagram of an exemplary controller 22 that may be used by the laser system 10 according to some embodiments. Controller 22 typically includes at least one processor 52 which may communicate with a number of peripheral devices via a bus subsystem 54. These peripheral devices may include a storage subsystem 56, comprising a memory subsystem 58 and a file storage subsystem 60, user interface input devices 62, user interface output devices 64, and a network interface subsystem 66. Network interface subsystem 66 provides an interface to outside networks 68 and/or other devices. Network interface subsystem 66 includes one or more interfaces known in the arts, such as LAN, WLAN, Bluetooth, other wire and wireless interfaces, and so on.

User interface input devices 62 may include a keyboard, pointing devices such as a mouse, trackball, touch pad, or graphics tablet, a scanner, foot pedals, a joystick, a touch screen incorporated into a display, audio input devices such as voice recognition systems, microphones, and other types of input devices. In general, the term "input device" is intended to include a variety of conventional and proprietary devices and ways to input information into controller 22.

User interface output devices 64 may include a display subsystem, a printer, a fax machine, or non-visual displays such as audio output devices. The display subsystem may be a flat-panel device such as a liquid crystal display (LCD), a light emitting diode (LED) display, a touchscreen display, or the like. The display subsystem may also provide a non-visual display such as via audio output devices. In general, the term "output device" is intended to include a variety of conventional and proprietary devices and ways to output information from controller 22 to a user.

Storage subsystem 56 can store the basic programming and data constructs that provide the functionality of the various embodiments. For example, a database and modules implementing the functionality of the methods of the present embodiments, as described herein, may be stored in storage subsystem 56. These software modules are generally executed by processor 52. In a distributed environment, the software modules may be stored on a plurality of computer systems and executed by processors of the plurality of computer systems. Storage subsystem 56 typically comprises memory subsystem 58 and file storage subsystem 60.

Memory subsystem 58 typically includes a number of memories including a main random access memory (RAM) 70 for storage of instructions and data during program execution and a read only memory (ROM) 72 in which fixed instructions are stored. File storage subsystem 60 provides persistent (non-volatile) storage for program and data files. File storage subsystem 60 may include a hard disk drive along with associated removable media, a Compact Disk (CD) drive, an optical drive, DVD, solid-state memory, and/or other removable media. One or more of the drives may be located at remote locations on other connected computers at other sites coupled to controller 22. The modules implementing the functionality of some embodiments may be stored by file storage subsystem 60.

Bus subsystem 54 provides a mechanism for letting the various components and subsystems of controller 22 communicate with each other as intended. The various subsystems and components of controller 22 need not be at the same physical location but may be distributed at various locations within a distributed network. Although bus subsystem 54 is shown schematically as a single bus, alternate embodiments of the bus subsystem may utilize multiple busses.

Due to the ever-changing nature of computers and networks, the description of controller 22 depicted in FIG. 4 is intended only as an example for purposes of illustrating only one embodiment. Many other configurations of controller 22, having more or fewer components than those depicted in FIG. 4, are possible.

As should be understood by those of skill in the art, additional components and subsystems may be included with laser system 10. For example, spatial and/or temporal integrators may be included to control the distribution of energy within the laser beam, as described in U.S. Pat. No. 5,646,791, which is incorporated herein by reference. Ablation effluent evacuators/filters, aspirators, and other ancillary components of the surgical laser system are known in the art, and may be included in the system. In addition, an imaging device or system may be used to guide the laser beam. Further details of suitable components of subsystems that can be incorporated into an ophthalmic laser system for performing the procedures described here can be found in commonly-assigned U.S. Pat. Nos. 4,665,913, 4,669,466, 4,732,148, 4,770,172, 4,773,414, 5,207,668, 5,108,388, 5,219,343, 5,646,791, 5,163,934, 8,394,084, 8,403,921, 8,690,862, 8,709,001, U.S. application Ser. No. 12/987,069, filed Jan. 7, 2011, and U.S. application Ser. No. 13/798,457 filed Mar. 13, 2013, which are incorporated herein by reference.

In an embodiment, the laser surgery system 10 includes a femtosecond oscillator-based laser operating in the MHz range, for example, 10 MHz, for example, from several MHz to tens of MHz. For ophthalmic applications, the XY-scanner 28 may utilize a pair of scanning mirrors or other optics (not shown) to angularly deflect and scan the pulsed laser beam 18. For example, scanning mirrors driven by galvanometers may be employed, each scanning the pulsed laser beam 18 along one of two orthogonal axes. A focusing objective (not shown), whether one lens or several lenses, images the pulsed laser beam onto a focal plane of the laser surgery system 10. The focal point of the pulsed laser beam 18 may thus be scanned in two dimensions (e.g., the X-axis and the Y-axis) within the focal plane of the laser surgery system 10. Scanning along a third dimension, i.e., moving the focal plane along an optical axis (e.g., the Z-axis), may be achieved by moving the focusing objective, or one or more lenses within the focusing objective, along the optical axis. It is noted that in many embodiments, the XY-scanner 28 deflects the pulse laser beam 18 to form a scan line.

Figure 5:
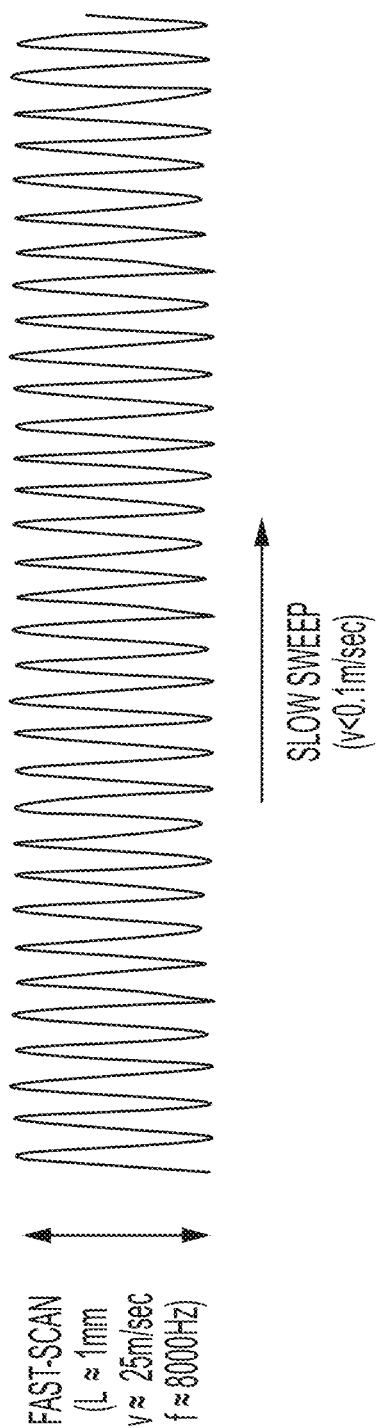
FIG. 5 illustrates an exemplary scanning of a surgical ophthalmic laser system according to some embodiments.

In other embodiments, the beam scanning can be realized with a "fast-scan-slow-sweep" scanning scheme. The scheme consists of two scanning mechanisms: first, a high frequency fast scanner is used to produce a short, fast scan line (e.g., a resonant scanner 21 of FIG. 3); second, the fast scan line is slowly swept by much slower X, Y, and Z scan mechanisms. FIG. 5 illustrates a scanning example of a laser system 10 using an 8 kHz resonant scanner 21 to produce a scan line of about 1 mm and a scan speed of about 25 m/sec, and X, Y, and Z scan mechanisms with the scan speed smaller than 0.1 m/sec. The fast scan line may be perpendicular to the optical beam propagation direction, i.e., it is always parallel to the XY plane. The trajectory of the slow sweep can be any three dimensional curve drawn by the X, Y, and Z scanning devices (e.g., XY-scanner 28 and Z-scanner 20). An advantage of the "fast-scan-slow-sweep" scanning scheme is that it only uses small field optics (e.g., a field diameter of 1.5 mm) which can achieve high focus quality at relatively low cost. The large surgical field (e.g., a field diameter of 10 mm or greater) is achieved with the XY-scanner, which may be unlimited.

Figure 6:
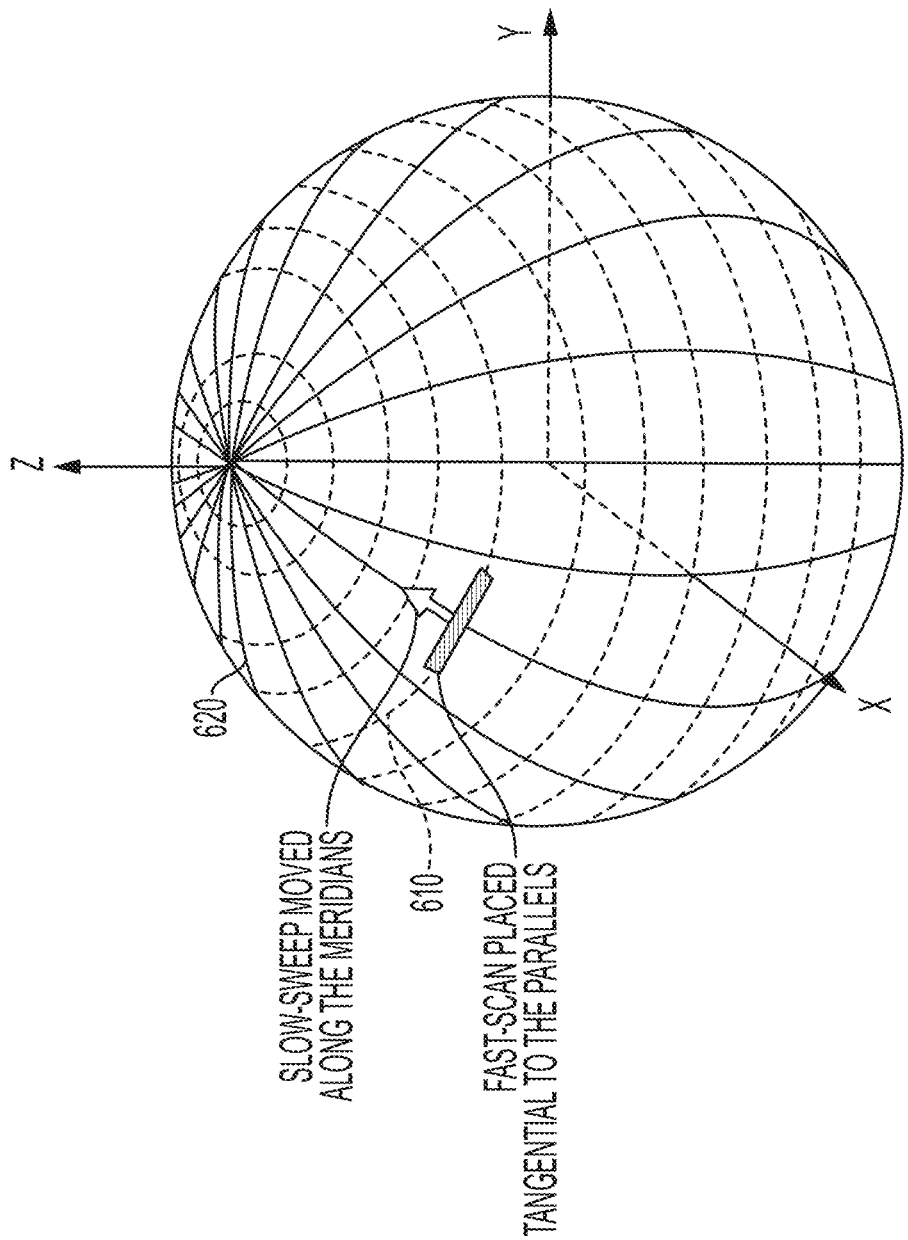
FIG. 6 illustrates an exemplary lenticular incision using a fast-scan-slow-sweep scheme of a surgical ophthalmic laser system according to some embodiments.

In another embodiment shown in FIG. 6, the laser system 10 creates a smooth lenticular cut using the "fast-scan-slow-sweep" scanning scheme under a preferred procedure. First, in a three dimensional lenticular cut, the fast scan line is preferably placed tangential to the parallels of latitude 610. For example, in the miniaturized flap maker laser system 10 of FIG. 3, this can be realized by adjusting a prism 23 to the corresponding orientations via software, e.g., via the controller 22. Second, the slow sweep trajectory preferably moves along the meridians of longitude 620. For example, in the miniaturized flap maker system of FIG. 3, this can be done by coordinating the XY scanner 28, and the Fast-Z scanner 20 via the software, e.g., via the controller 22. The procedure starts with the scan line being parallel to the XY plane, and sweeps through the apex of the lens, following the curvature with the largest diameter (see also FIG. 8). With this preferred procedure, there are no vertical "steps" in the dissection, and vertical side cuts are eliminated. As will be analyzed herein below, the deviations between the laser focus locations and the intended spherical surface dissections are also minimized.

Figure 7:
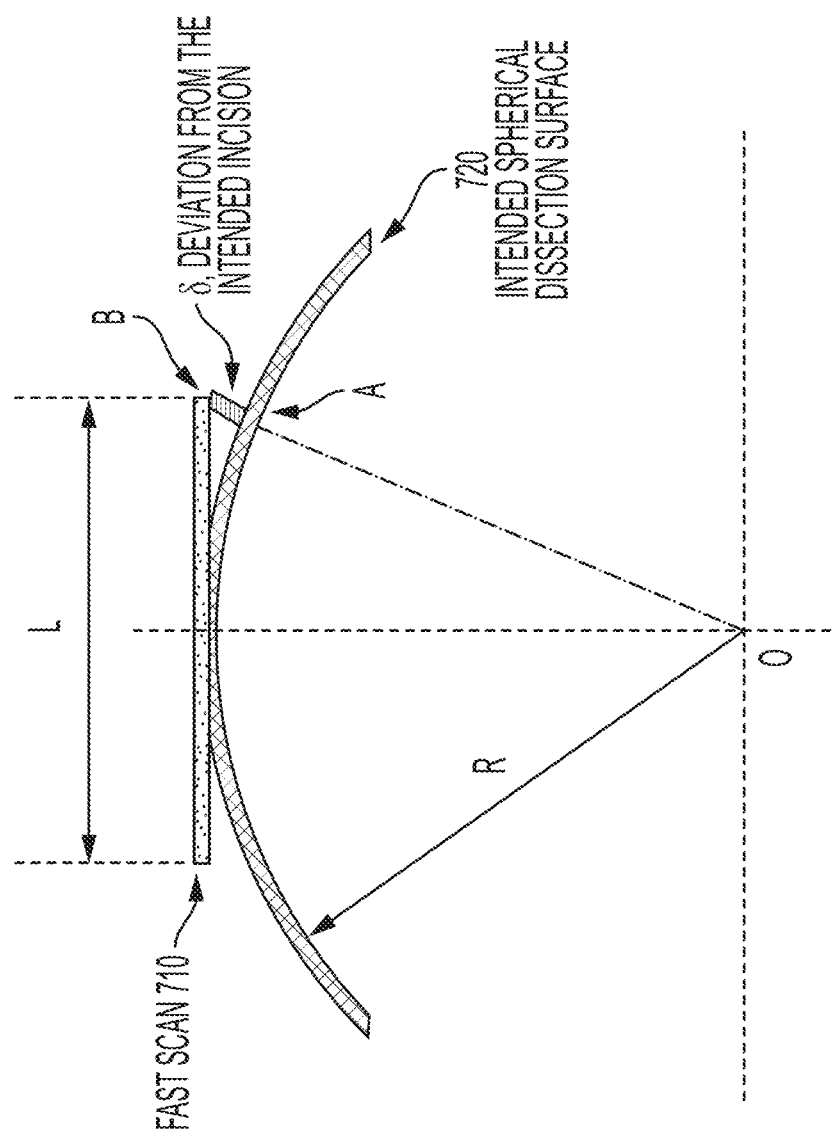
FIG. 7 illustrates a geometric relation between a fast scan line and an intended spherical dissection surface of a surgical ophthalmic laser system according to some embodiments.

FIG. 7 shows the geometric relation between the fast scan line 710 and the intended spherical dissection surface 720, e.g., of a lens, especially the distance deviation (δ) between the end point B of the scan line 720 and point A on the intended dissection surface 720. The maximum deviation δ is the distance between point A and point B, and is given by $$\delta = \sqrt{R^2 + \frac{L^2}{4}} - R = \frac{L^2}{8R}, \qquad \text{equation (1),}$$

where R is greater than L. R is the radius of curvature of the surface dissection 720, and L is the length of the fast scan.

In an exemplary case of myopic correction, the radius of curvature of the surface dissection may be determined by the amount of correction, ΔD, using the following equation $$\Delta D = \frac{(n-1)}{R_1} + \frac{(n-1)}{R_2}, \qquad \text{equation (2),}$$

where n=1.376, which is the refractive index of cornea, and $R_1$ and $R_2$ (may also be referred herein as $R_t$ and $R_b$) are the radii of curvature for the top surface and bottom surface of a lenticular incision, respectively. For a lenticular incision with $R_1=R_2=R$ (the two dissection surface are equal for them to physically match and be in contact), we have $$R = \frac{2(n-1)}{\Delta D}, \qquad \text{equation (3).}$$

Figure 8:
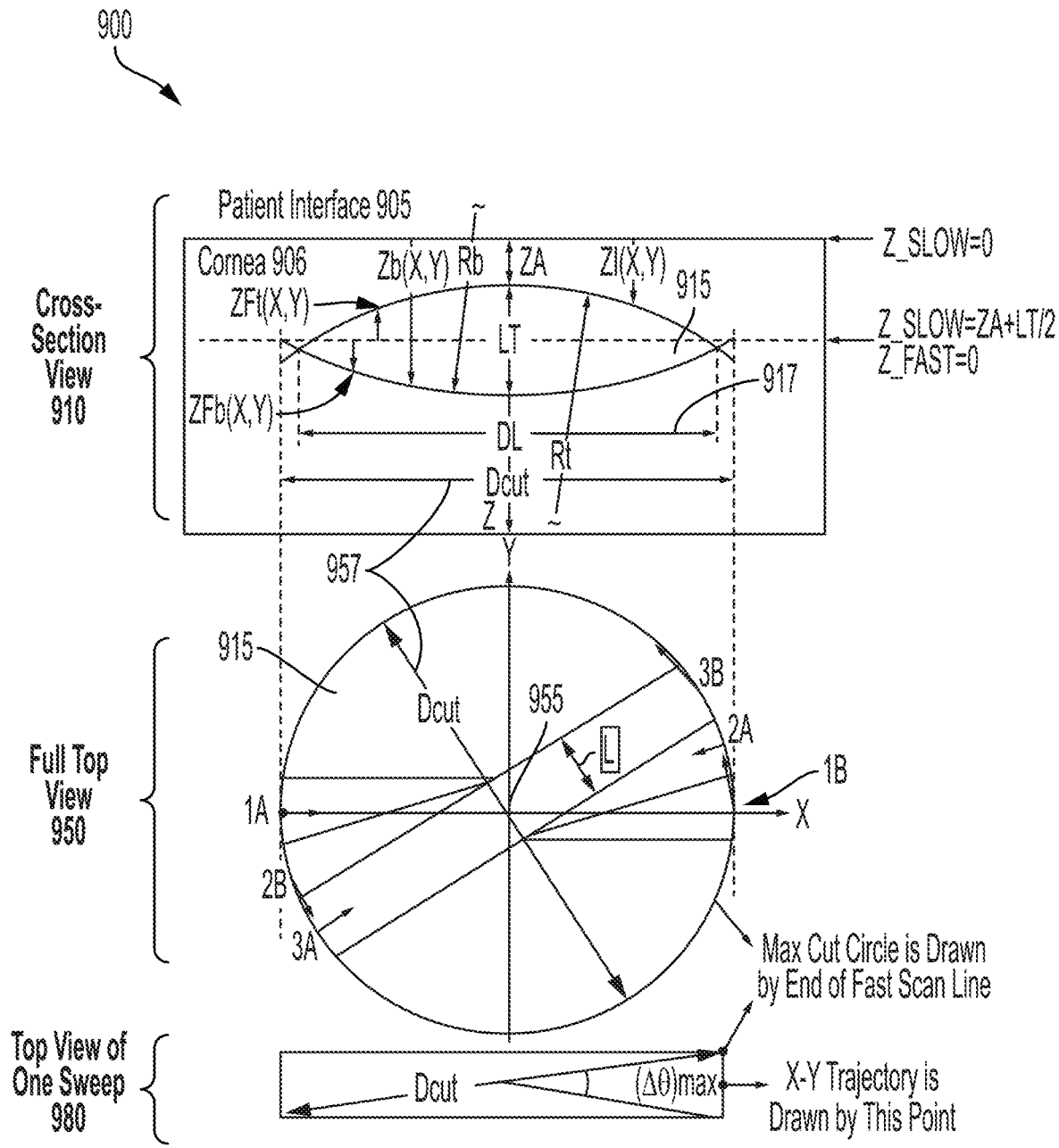
FIG. 8 illustrates an exemplary lenticular incision using a surgical ophthalmic laser system according to some embodiments.

In an embodiment, FIG. 8 shows an exemplary lenticular incision 900 for extraction using the laser system 10. FIG. 8 shows an exemplary cross-sectional view 910 illustrating a patient interface 905 (or patient interface 31 as shown in FIG. 3), cornea 906, and lenticular incision volume 915, which will be referred herein as lens to be extracted. Rt and Rb are the radii of curvature for the top surface and bottom surface of a lenticular incision, respectively. ZFt (Zt) is the depth of the top surface of the lenticular incision. ZFb (Zb) is the depth of the bottom surface of the lenticular incision. The Z depths may be calculated based on the respective radii. LT is the lens thickness at the lens apex, or center thickness of the lens. ZA is depth of the lens apex. DL is the diameter of the lenticular incision, or the lens. {Z_SLOW=0} is the Z reference position before the laser system 10 calculates and sets Z_SLOW, e.g., {Z_SLOW=ZA+LT/2} the center depth of the lens, which remains fixed for the duration of the incision procedure. Z_SLOW may then be the reference position for the Z-scanner for top and bottom incision surfaces. In an embodiment, the diameter of the lens may be received from an operator of the laser system 10, or may be calculated by the laser system 10. The thickness of the lens may be determined, for example, by the total amount of correction (e.g., diopter) and the diameter of the lens.

A top view 950 of the lenticular incision 900 illustrates three exemplary sweeps (1A to 1B), (2A to 2B) and (3A to 3B), with each sweep going through (i.e., going over) the lenticular incision apex 955. The incision, or cut, diameter 957 ($D_{CUT}$) should be equal to or greater than the to-be-extracted lenticular incision diameter 917 (DL). A top view 980 shows the top view of one exemplary sweep. In an embodiment, the lenticular incision is performed in the following steps:

1. Calculate the radius of curvature based on the amount of correction, e.g., a myopic correction.
2. Select the diameter for the lenticular incision to be extracted.
3. Perform the side incision first (not shown) to provide a vent for gas that can be produced in the lenticular surface dissections. This is also the incision for the entry of forceps and for lens extraction.
4. Perform bottom surface dissection (the lower dissection as shown in cross-sectional view 910). In doing so, the fast scan line is preferably kept tangential to the parallels of latitude, and the trajectory of the slow sweep drawn by X, Y, and Z scanning devices moves along the meridians of longitude (near south pole in a sequence of 1A→1B (first sweep of lenticular cut), 2A→2B (second sweep of lenticular cut), 3A→3B (third sweep of lenticular cut), and so on, until the full bottom dissection surface is generated.
5. Perform the top surface dissection (the upper dissection as shown in the cross-sectional view 910) in a similar manner as the bottom dissection is done. It is noted that the bottom dissection is done first. Otherwise, the bubble generated during the top dissection will block the laser beam in making the bottom dissection.

For illustrative purposes, in a myopic correction of ΔD=10 diopter (i.e., 1/m), using equation (3), R=75.2 mm, which is indeed much greater than the length L of the fast scan. Assuming a reasonable scan line length of L=1 mm, using equation (1), the deviation δ≈1.7 μm. This deviation is thus very small. For comparison purpose, the depth of focus of a one micron (FWHM) spot size at 1 μm wavelength is about ±3 μm, meaning the length of focus is greater than the deviation δ.

Figure 9:
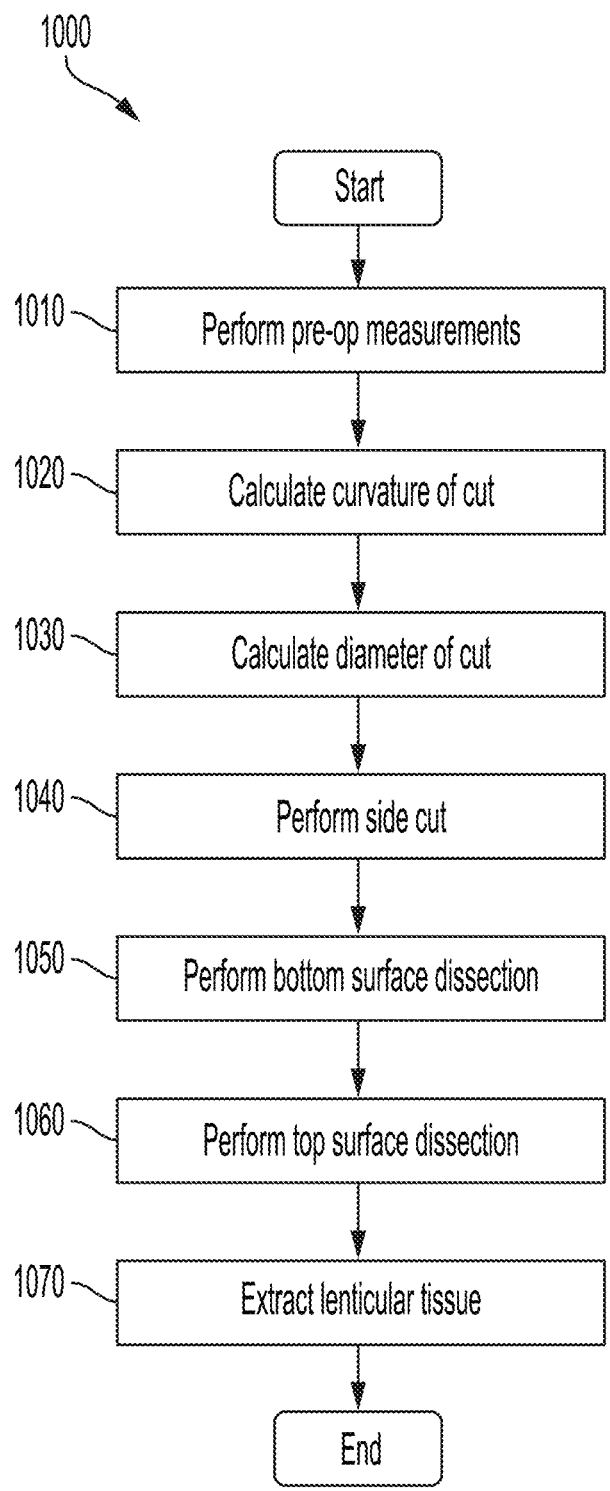
FIG. 9 is a flowchart illustrating a process according to some embodiments.
Figure 10:
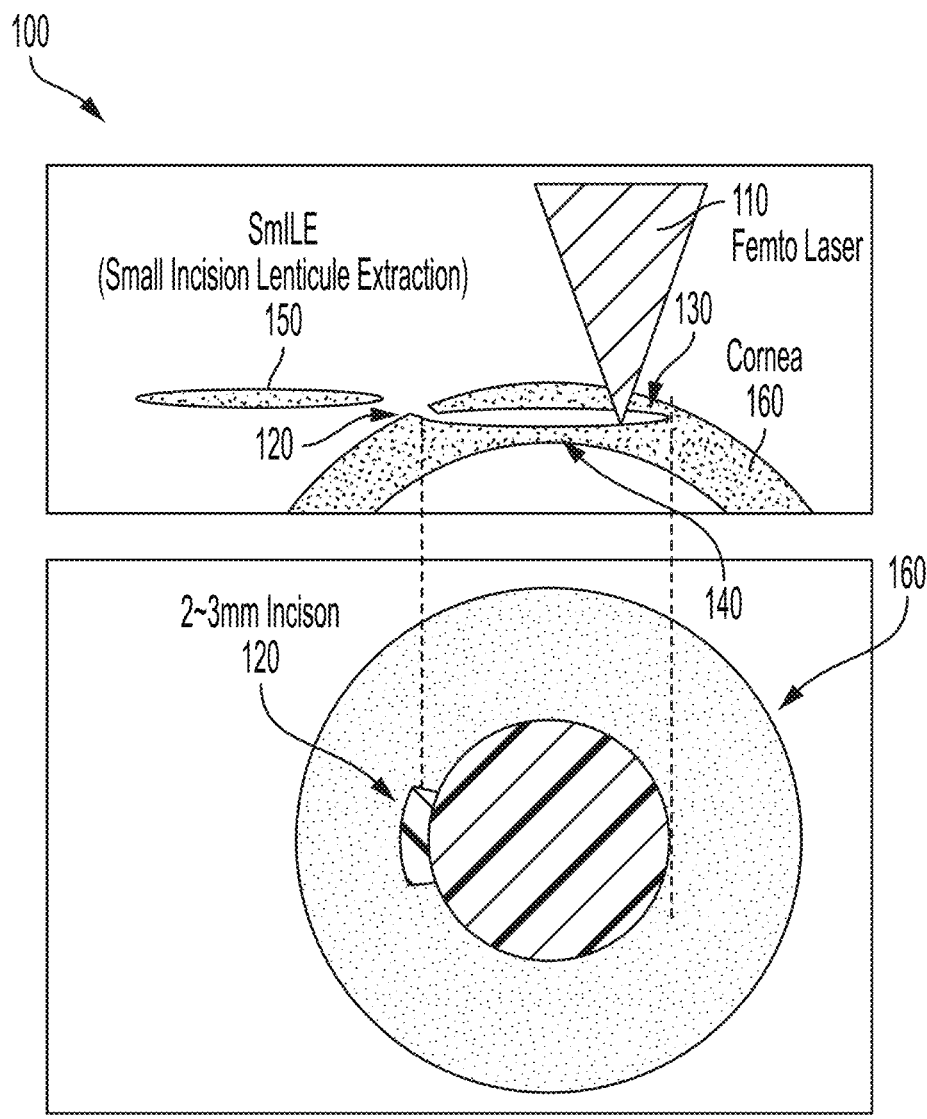
FIG. 10 illustrates an example Small Incision Lenticule Extraction procedure.

FIG. 9 illustrates a process 1000 of the laser system 10 according to an embodiment. The laser system 10 may start a surgical procedure performing pre-operation measurements (Action Block 1010). For example, in an ophthalmologic surgery for myopic correction, the myopic diopter is determined, the SLOW_Z position is determined, and so on. The laser system 10 calculates the radius of curvature based on the amount of correction, e.g., the myopic correction determined in pre-operation measurements (Action Block 1020), as shown, for example, in equations (2) and (3) above. The laser system 10 calculates the diameter of the incision (Action Block 1030), as shown by $D_{CUT}$ in FIG. 8. $D_{CUT}$ is equal to or greater than the diameter of the to-be-extracted lenticule (DL in FIG. 8). The laser system 10 first performs side incision to provide a vent for gas that can be produced in the lenticular surface dissections, and for tissue extraction later on (Action Block 1040). The laser system 10 then performs the bottom lenticular surface dissection (Action Block 1050) before performing the top lenticular surface dissection (Action Block 1060). The lenticular tissue is then extracted (Action Block 1070).

In other embodiments, the laser system 10 may also be used to produce other three-dimensional surface shapes, including toric surfaces for correcting hyperopia and astigmatism. The laser system 10 may also be used for laser material processing and micromachining for other transparent materials. Correction of hyperopia by the laser system 10 is discussed in detail below.

Figure 11:
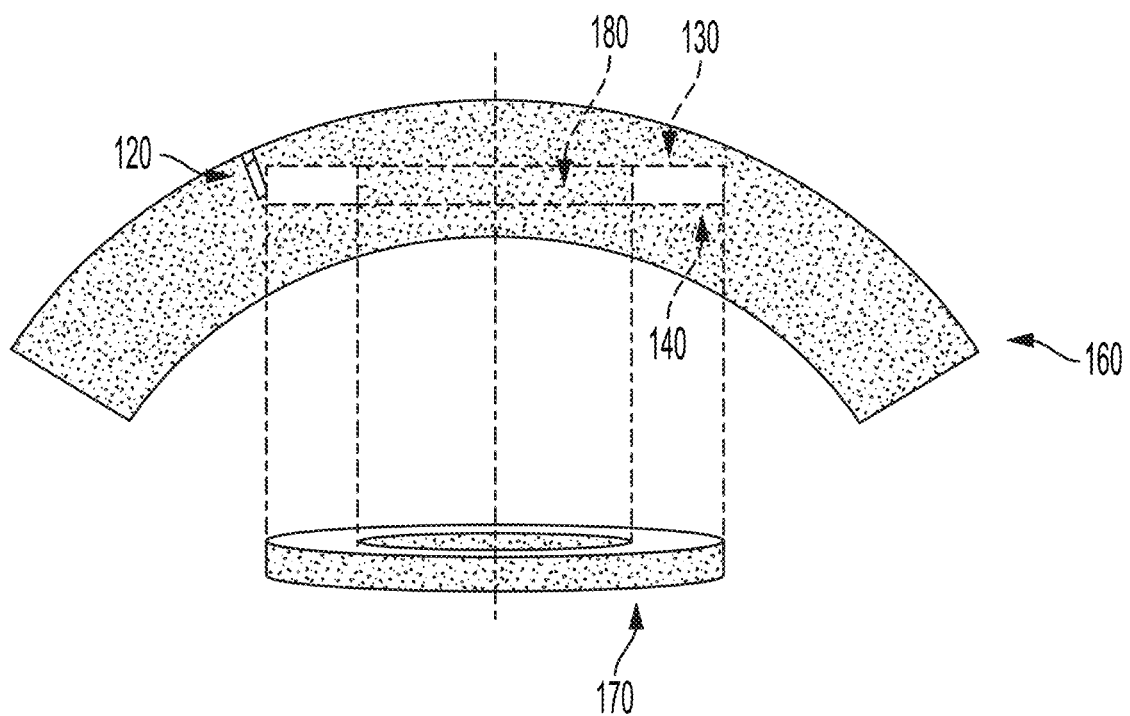
FIG. 11 illustrates another example Small Incision Lenticule Extraction procedure.

Conventional laser surgery methods to correct hyperopia utilize cut patterns including ring-shaped incision patterns that steepen the curvature of a cornea. However, FIG. 11 illustrates why utilizing these patterns using SMILE is impractical and unfeasible. The cross-sectional view of the cornea 160 in FIG. 11 includes a sidecut 120, an upper surface cut 130, lower surface cut 140 and a ring-shaped cut 170 generated by a SMILE procedure. However, the cornea 160 maintains an uncut annular center portion 180 that remains attached to an anterior portion and posterior portion of the cornea 160.

This cut pattern is geometrically problematic as the clean removal of the ring cut 170 through the side cut 120 as a single ring is impeded by the center portion 180. Whereas a flap provided in a LASIK procedure allows a ring shape to be easily extracted, the use of a sidecut without a flap prevents the ring-shaped stroma material from being extracted from the tunnel like incision without breaking apart. Thus, a ring-shaped lenticule is not suitable for correcting hyperopia using the SMILE procedure since the ring cut 170 will break up unpredictably during removal through the side cut 120.

Some LASIK procedures correct hyperopia by removing cornea stroma material to increase the steepness of the cornea. For example, outward portions of the cornea are cut and removed while a center portion remains untouched except for the flap. Once the flap is folded back over, the flap fills the void vacated by the removed cornea stroma material and merges with the cornea. The cornea thus becomes steeper and a desired vision correction is achieved. However, the curve of the flap does not match the curve of the cornea such that the merger of the flap and cornea creates folds in the stroma that increase light scattering and create undesirable aberrations.

Figure 12:
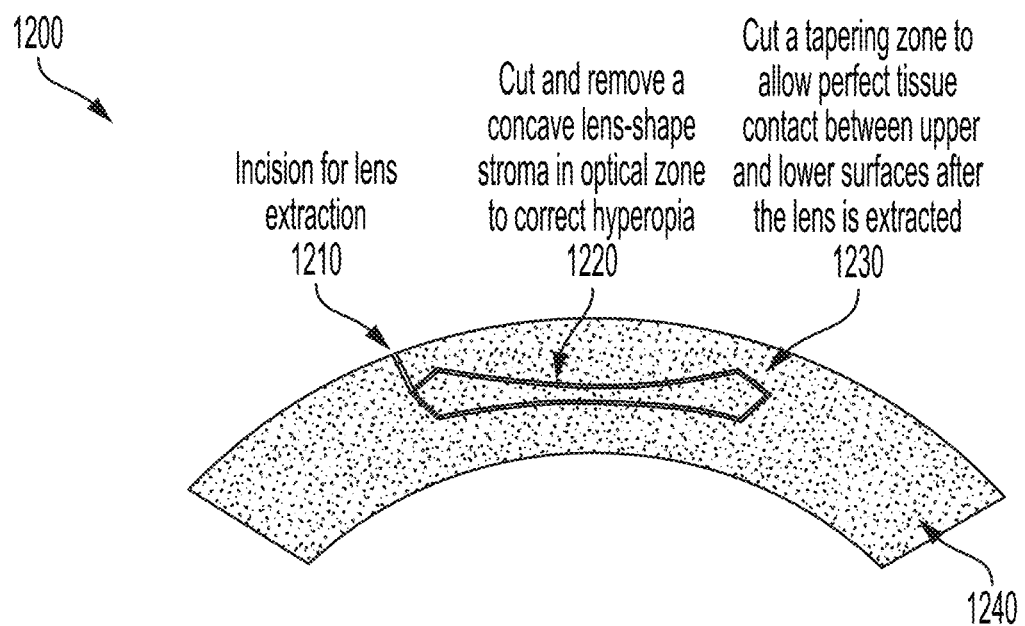
FIG. 12 illustrates an exemplary lenticular incision process according to some embodiments.

The embodiments described herein overcome these limitations. FIG. 12 illustrates an exemplary lenticular incision 1200 that steepens the cornea by cutting and removing a symmetric concave lens-shaped stroma material from a cornea 1240. From an optical focus power perspective, the concave shape of the lenticule 1220 is equivalent to steepening the cornea or adding a convex lens in front of the eye.

Furthermore, extraction of the lenticule 1220 as a whole piece through a sidecut incision 1210 is assured and improved over a ring-shape cut, or a tunnel-like cut, or a toric cut. The incision includes a peripheral portion 1230 or tapering portion providing ideal merging of the cornea after the lenticule 1220 is extracted without folding in a top surface or bottom surface.

Figure 13:
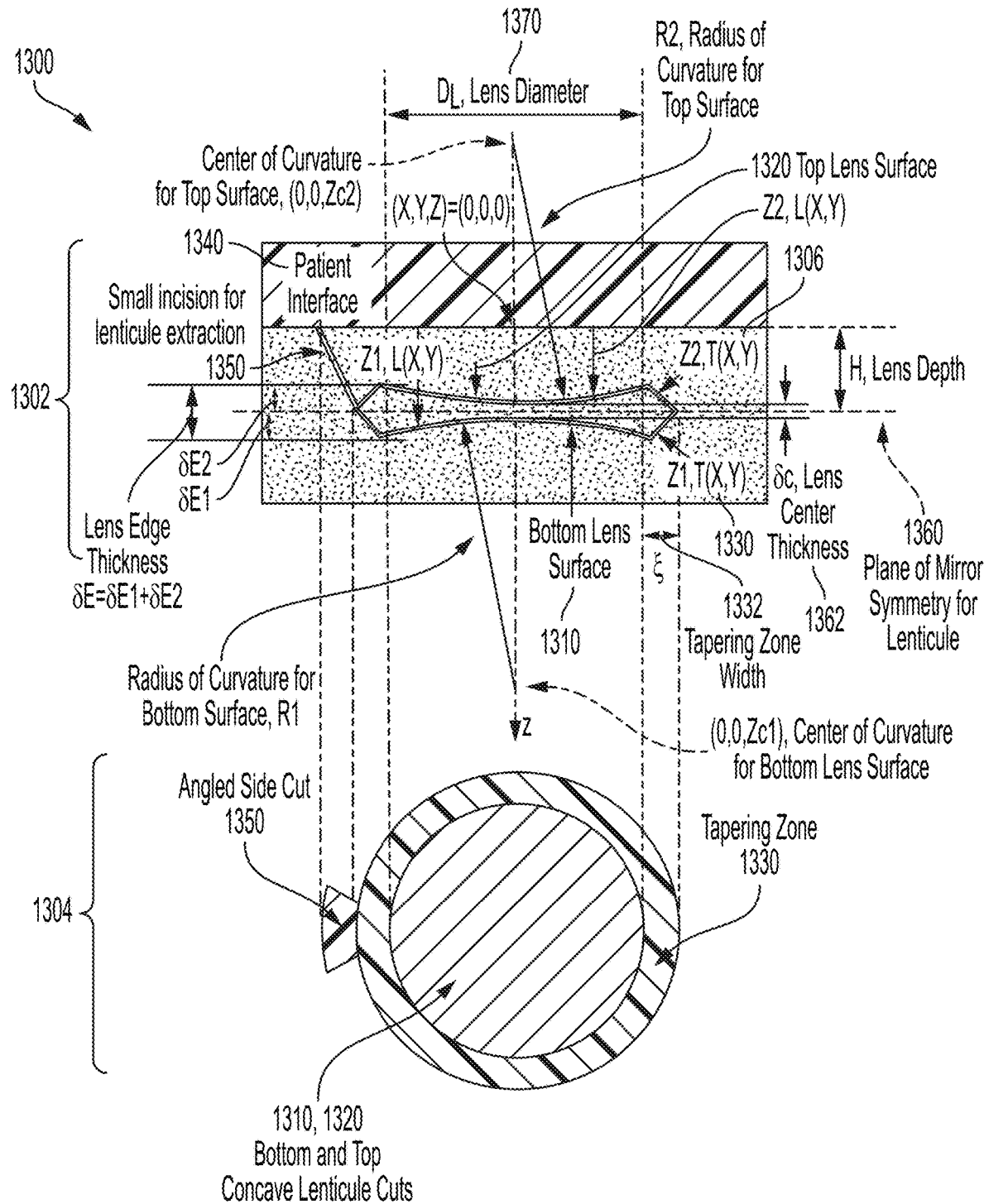
FIG. 13 illustrates an exemplary lenticular incision using a surgical ophthalmic laser system according to some embodiments.

FIG. 13 illustrates an exemplary lenticular incision 1300 using a surgical ophthalmic laser system according to an embodiment of the present embodiments. For example, SMILE techniques may be applied in conjunction with FIG. 13 to treat hyperopia using a sub-nanosecond laser. A cross-sectional view 1302 and top view 1304 are provided of the lenticule cuts 1310, 1320 and side cut 1350. In FIG. 13, a patient interface 1340 is pressed against a cornea 1306. The lenticular incision includes a bottom lens surface 1310 and a top lens surface 1320. The bottom surface 1310 includes a radius of curvature R1 and the top surface 1320 includes a radius of curvature R2.

A side cut 1350 is performed first to provide a path for gas to vent to prevent the formation of bubbles. A bottom surface cut 1310 is then performed prior to performing a top surface cut 1320 to prevent the cutting beam from being blocked by bubbles generated by previous cornea dissection. The top and bottom surface cuts each include a central portion and a peripheral portion. The central portions are concave while the peripheral portions of the top and bottom cuts tapers (diminishes) towards each other to meet. The tapering peripheral portions minimize light scattering at the edges and further optimizes the matching of the cut surfaces and prevent folding after the lenticule has been removed.

As shown in FIG. 13, the thickest portion of the cut is provided at the boundary of the taper portion and the concave portion. For the top and bottom surfaces to match after lens extraction, the bottom and top surfaces are preferably mirror symmetric about a plane 1360.

These exemplary lenticular incisions allow lenticular tissue to be extracted in a single unbroken piece through the sidecut. The taper of the peripheral portions allows smooth extraction through the sidecut as a gradual slope is provided. The peripheral portions also support the merging of the top and bottom portions of the cornea as a top surface and bottom surface compress back together to form a smooth merge. Without a taper to the peripheral portions, the apex of the central portions would never merge and would form a permanent gap.

A concave lens cut includes a top concave lenticular incision and a bottom concave lenticular incision of a lens in the subject's eye. The concave lens cut may include at least one of a spherical surface, a cylindrical component, and any high order component. The top concave lenticular incision and the bottom concave lenticular incision may be mirror symmetric or nearly mirror symmetric to each other so long as the merging of the top surface and bottom surface does not create folding.

The system may operate with a laser having a wavelength in a range between 350 nanometer and 1100 nanometer and a pulse width in a range between 10 femtosecond and 1 nanosecond.

In prior art solutions, a top layer cut is longer than a bottom layer cut. Under this configuration, the top and bottom cornea portions do not ideally merge as the top surface must fold in and compress in order to merge with shorter layer cut. With this fold created by the dissection, light scattering is increased. In contrast, a mirror symmetric cut along a center line allows ideal merge with no folding between a top layer and bottom layer. Consequently, there is less light scattering.

A lens edge thickness is given by $\delta_E$, $\delta_{E1}$, $\delta_{E2}$. A lens depth H is given as a distance between an anterior of the cornea 1306 and the plane 1360. The bottom surface 1310 and top surface 1320 have a lens diameter $D_L$, a lens center thickness $\delta c$ and a shape defined by respective curves $Z_{1,L}(x,y)$ and $Z_{2,L}(x,y)$. In order to minimize the amount of dissected cornea stroma material removed, the central thickness $\delta c$ should be minimized. For example, the central thickness may be a few μm, which can be achieved by using a laser beam with a high numerical aperture (such as NA=0.6).

Each of the bottom lens surface cut 1310 and the top lens surface cut 1320 includes a tapering zone 1330 along a periphery of the cuts. The tapering zone 1330 is defined by a tapering zone width and the curves $Z_{1,T}(x,y)$ and $Z_{2,T}(x,y)$.

A sidecut 1350 is provided from a surface of the cornea to the tapering zone 1330 for removal of the lenticule. The sidecut may meet the tapering zone 1330 on the mirror plane 1360 or other suitable extraction point.

With these parameters as described and illustrated, a set of equations are provided below that determine the three-dimensional shape of the lenticular cuts, assuming that the desired correction is purely defocus:

$$Z_{1,L}(x, y) = H + \frac{\delta_C}{2} + R_1 - \sqrt{R_1^2 - x^2 - y^2} \text{ for } \sqrt{x^2 + y^2} \leq \frac{D_L}{2} \quad \text{Eq. (4)}$$

-continued $$Z_{2,L}(x, y) = H - \frac{\delta_C}{2} - R_2 + \sqrt{R_2^2 - x^2 - y^2} \text{ for } \sqrt{x^2 + y^2} \leq \frac{D_L}{2} \quad \text{Eq. (5)}$$

$$Z_{1,T}(x, y) = H + \delta_{E1} - \left(\sqrt{x^2 + y^2} - \frac{D_L}{2}\right) \cdot \frac{\delta_{E1}}{\xi} \text{ for } \frac{D_L}{2} \leq \quad \text{Eq. (6)}$$

$$\sqrt{x^2 + y^2} \leq \frac{D_L}{2} + \xi$$

$$Z_{2,T}(x, y) = H - \delta_{E2} + \left(\sqrt{x^2 + y^2} - \frac{D_L}{2}\right) \cdot \frac{\delta_{E2}}{\xi} \text{ for } \frac{D_L}{2} \leq \quad \text{Eq. (7)}$$

$$\sqrt{x^2 + y^2} \leq \frac{D_L}{2} + \xi$$

$$\delta_{E1} = \frac{\delta_C}{2} + R_1 - \sqrt{R_1^2 - \left(\frac{D_L}{2}\right)^2} \quad \text{Eq. (8)}$$

$$\delta_{E2} = \frac{\delta_C}{2} + R_2 - \sqrt{R_2^2 - \left(\frac{D_L}{2}\right)^2} \quad \text{Eq. (9)}$$

The shape and dimensions of the cuts may include additional correction for higher order aberrations and may be computed from measured vision errors. In some embodiments, approximately 50% of the total hyperopic correction is applied to each of the two mutually mirror-imaged cut surfaces.

It is noted that the thickest portion of the concave lens cut is provided at the intersection of the tapering zone and the concave lens cuts which correspond to a portion of the cornea that is thicker than a center portion of the cornea. Consequently, from the standpoint of cornea thickness, correcting hyperopia is more tolerable than correcting myopia, where the thicker portion of the lens to be removed is at the center of the cornea, corresponding to a thinner portion of the cornea.

The shape of the tapering zone 1330 need not be linear in shape. The tapering zone may be curved or any shape that minimizes light scattering at the cutting junctions and optimizes the matching of the two cut surfaces after lens extraction. The peripheral zone may be linear or a higher order polynomial.

Some embodiments apply to single-spot scanning methods applied in femtosecond laser systems. The embodiments also apply to cornea incisions using UV 355 nm sub-nanosecond lasers.

For illustrative purposes, Equations (2), (8) and (9) are used to estimate the thickness of the concave lens. In a hyperopic correction of ΔD=5 diopter (which is high end values for LASIK hyperopia procedures) and assuming that a symmetric shape of the lenticule is selected, $R_1 = R_2 = 150.4$ mm. Assuming $D_L = 7.0$ mm and $\delta_C = 10$ μm, then $\delta_E = \delta_{E1} + \delta_{E2} \approx \delta_C + D_L^2 \cdot \Delta D / [8(n-1)] \approx 92$ μm.

Figure 14:
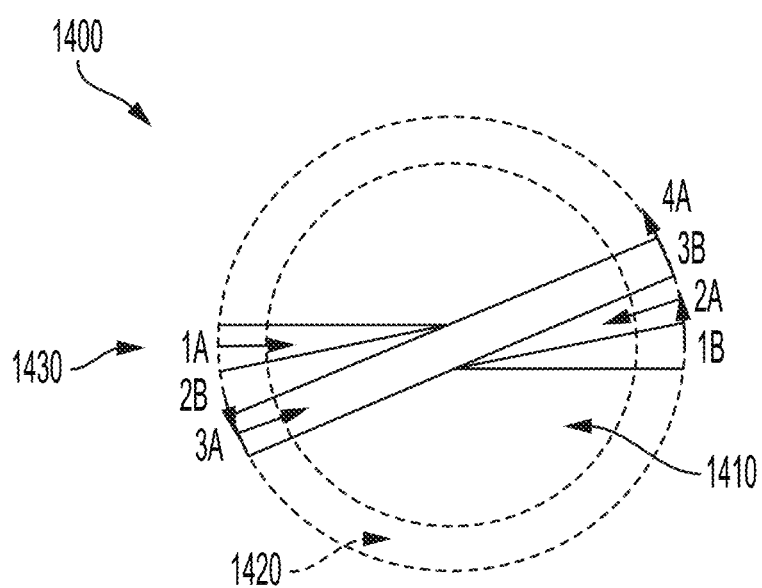
FIG. 14 illustrates an exemplary scanning process using a surgical ophthalmic laser system according to some embodiments.

FIG. 14 illustrates an exemplary scanning process 1400 using a surgical ophthalmic laser system according to some embodiments. FIG. 14 illustrates another embodiment of the "Fast-Scan-Slow-Sweep" scanning described previously. While performing an XY scan, Z values can be calculated from Eqs. (1)-(9), and the desired three-dimensional concave lens-shape cutting surfaces may be generated.

A top view of the lenticular incision illustrates three exemplary sweeps 1430 (1A to 1B), (2A to 2B) and (3A to 3B), with each sweep going through (i.e., going over) the concave lenticular incision 1410 and tapering zone 1420. In an embodiment, the lenticular incision is performed in the following steps:
1. Calculate the radius of curvature based on the amount of correction, e.g., a hyperopic correction.
2. Select the diameter for the lenticular incision to be extracted.
3. Calculate the shape of the lenticular incisions (concave surface and taper).
4. Perform the side incision first (not shown) to provide a vent for gas that can be produced in the lenticular surface dissections. This is also the incision for the entry of forceps and for lens extraction.
5. Perform bottom surface dissection (the bottom dissection 1310 as shown in cross-sectional view). In doing so, the fast scan line is preferably kept tangential to the parallels of latitude, and the trajectory of the slow sweep drawn by X, Y, and Z scanning devices moves along the meridians of longitude (near south pole in a sequence of 1A→1B (first sweep of lenticular cut), 2A→2B (second sweep of lenticular cut), 3A→3B (third sweep of lenticular cut), and so on (4A), until the full bottom dissection surface is generated.
6. Perform the top surface dissection 1320 in a similar manner as the bottom dissection is done. It is noted that the bottom dissection is done first. Otherwise, the bubble generated during the top dissection will block the laser beam in making the bottom dissection.

Improved Parameter Examples

Certain example parameters for using the femtosecond laser in intra-stromal corneal incisions may improve results. Using the laser described herein outside of the laser parameters described below may result in undesirable consequences such as melted corneal tissue or tissue bridges left in cutting beds even after treatment. Neither of these effects are desirable, and by utilizing the parameters below, with the femtosecond laser described above, results may be reached for treatment which avoid these effects. Thus, using the parameters here, the laser may be used to create a smooth incision in the cornea and improve treatment.

As discussed above, the femtosecond laser beam may be directed into an intrastromal corneal layer of a patient for treatment. The system may pre-compensate dispersion of the laser beam path so as to focus the laser beam into a focal point to disrupt cells in the intrastromal corneal layer. This laser beam focus may be moved to create a pattern of spaced focal points inside the intrastromal corneal layer thus incising a lens with the spaced focal points. And as the xy scan pattern is continuous in the systems described above, oscillating the beam in a given distance producing a scan line for treatment. The z depth of the focal points may be adjusted along with the xy position to allow the oscillating beam to incise the cornea.

Figure 15:
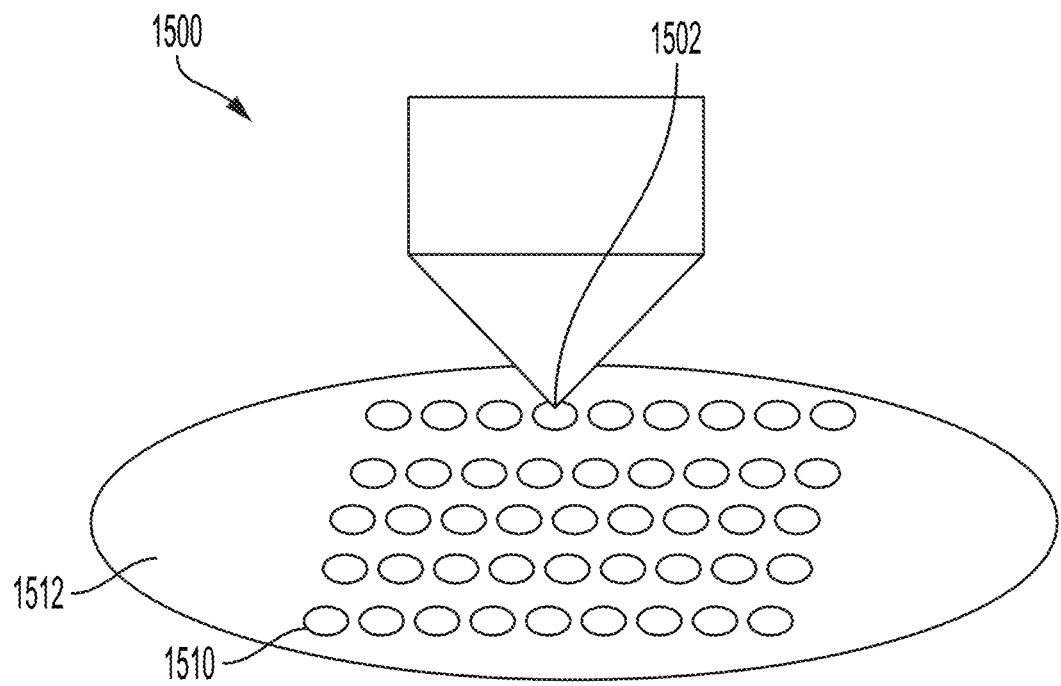
FIG. 15 illustrates an exemplary scanning pattern using a surgical ophthalmic laser system according to some embodiments.

FIG. 15 illustrates an example pattern 1500 of focused laser 1502 spots 1510. The example of FIG. 15 shows a cornea 1512 being treated as described herein, but the tissue that is treated could be any kind of tissue in the eye or elsewhere on the body.

It should be noted that all of the parameters listed below are specific to the laser beam at the spot focus 1502 itself. In other words, the laser beam may have different parameters within the laser system or within the various focus sub systems. These parameters listed below pertain to the focused laser beam spot at the treatment point.

Wavelength—wavelength of the femtosecond laser described above can be between 300 nm and 1100 nm. A preferred embodiment is between 1020 nm and 1065 nm.

Spot size—in diameter, spot size of each individually focused laser beam focal spot could be between 0.3 μm and 1.5 μm. A preferred spot size is near 1 μm in diameter.

Spot spacing—spot spacing of each individually focused laser beam focal spot, from center to center of individual spots, could be between 0.2 µm and 2 µm. In certain preferred embodiments, a spot spacing of less than 1 µm is used.

In the above examples, a laser beam focal spot size of 1 µm in diameter combined with a laser beam focal spot spacing of less than 1 µm results in overlapping spots. And as the laser beam focal spot causes tissue disruption in a cornea, for example, forming a bubble in the tissue, the bubbles may be even greater than 1 µm in diameter and overlap as well. Using the example laser and laser parameters described here, however, this overlapping of focal spots and bubbles is an acceptable spacing and spot size because of the energy parameters used. Overlapping focal spots using other lasers, or lasers with different parameters may result in excessive power into the eye, melting of tissue and other less desired effects.

Frequency—The system may utilize a laser beam having a frequency between 1 and 20 MHz. An example embodiment is a laser beam with a frequency of 10 MHz. Another example embodiment is 8 MHz.

Some example embodiments include using a resonant scanner to produce a scan line. In some examples the resonant scanner continuously scans while the laser system is in operation. Example frequencies for such a scan may be between 2,000 Hz and 20,000 Hz. Some example embodiments use 8,000 Hz.

Pulse width—the femtosecond laser described above may have a pulse width between 50 fs and 200 fs. A preferred embodiment is between 100 and 200 femtoseconds. A pulse width below 250 femtoseconds may produce optimal results.

In some embodiments, dispersion compensation may be used to achieve short pulse width at the focal point of the laser beam. Such dispersion compensation may include a glass compressor to introduce negative chirp.

Energy—the femtosecond laser described above has a smaller pulse width but higher peak power than other lasers currently available. But in comparison, the femtosecond laser total power may be less than other lasers with wider pulse width and lower peak power. Energy used in one spot may be between 20 nJ and 200 nJ. One example embodiment is between 70 nJ and 130 nJ.

Figure 16:
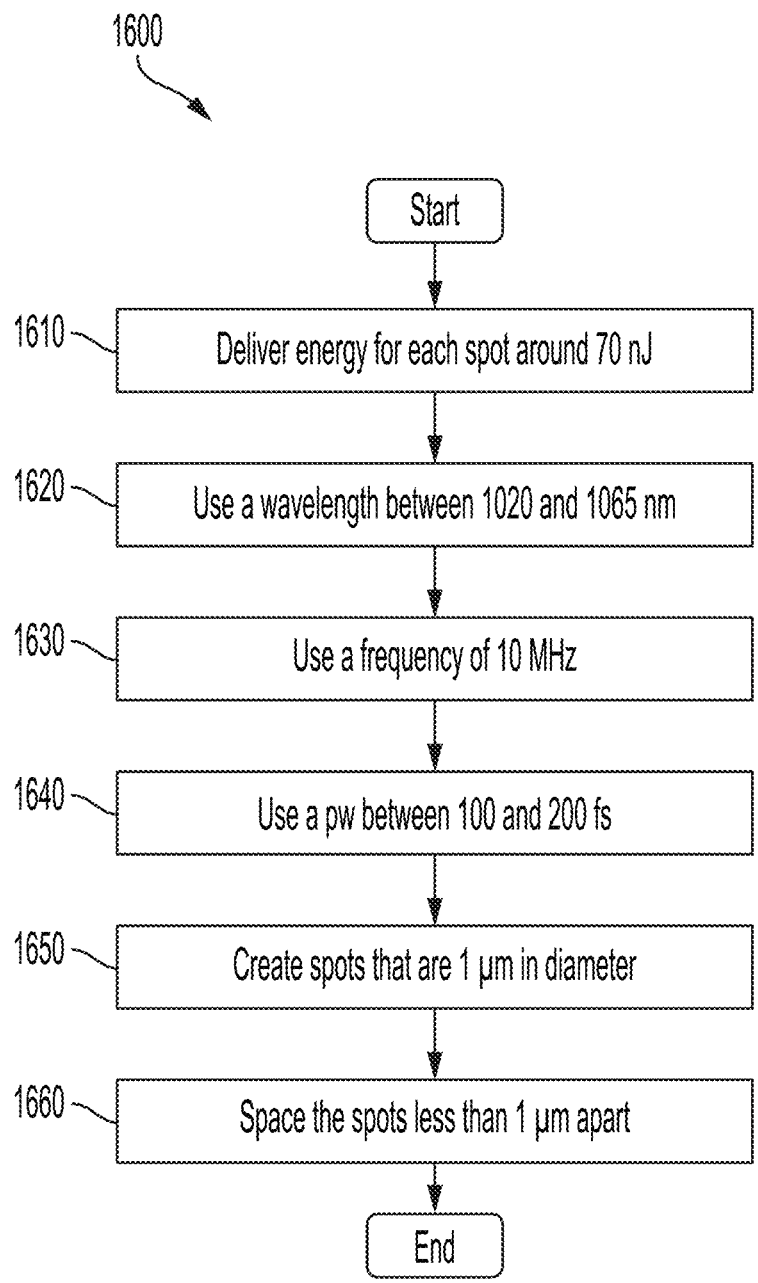
FIG. 16 is a flowchart with improved methods for lenticular incisions using a femtosecond laser according to some embodiments.

FIG. 16 is a flowchart illustrating an exemplary surgery process 1600 according to some embodiments. At the treatment site, the laser system is first set to limit the amount of total energy for an individual spot to around 70 nJ 1610. Next, at the treatment site, the wavelength of the laser is set to between 1020 and 1065 nm 1620. Next, at the treatment site, the frequency of the laser is set to 10 MHz 1630. Next, at the treatment site, the laser pulse width is set to between 100 and 200 femtoseconds 1640. Next, at the treatment site, spots are created that are 1 µm in diameter 1650. Finally, at the treatment site, the spots are spaced apart less than 1 µm 1660.

All patents and patent applications cited herein are hereby incorporated by reference in their entirety.

The use of the terms "a" and "an" and "the" and similar referents in the context of describing the embodiments (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate some embodiments and does not pose a limitation on the scope of some embodiments unless otherwise claimed. No language in the specification should be construed as indicating any non-claimed element as essential to the practice of the embodiments.

While certain illustrated embodiments of this disclosure have been shown and described in an exemplary form with a certain degree of particularity, those skilled in the art will understand that the embodiments are provided by way of example only, and that various variations can be made without departing from the spirit or scope of the embodiments. Thus, it is intended that this disclosure cover all modifications, alternative constructions, changes, substitutions, variations, as well as the combinations and arrangements of parts, structures, and steps that come within the spirit and scope of the embodiments as generally expressed by the following claims and their equivalents.

What is claimed is:

1. A method comprising:
    directing an ophthalmic surgical femtosecond pulsed laser beam into an intrastromal corneal layer of a patient, wherein at a position delivered to the intrastromal corneal layer, a wavelength of the laser is between 300 nm and 1100 nm, a pulse frequency of the laser is between 1 and 20 MHz, a pulse width of the laser is between 50 fs and 200 fs, and a pulse energy of the laser is between 20 nJ and 200 nJ;
    focusing the laser beam into a focal spot in the intrastromal corneal layer, wherein a spot size of the focal spot is between 0.3 µm and 1.5 µm in diameter;
    moving the laser beam to create a pattern of spaced focal spots inside the intrastromal corneal layer to disrupt cells in the intrastromal corneal layer, wherein a spot spacing between focal spots formed by temporally adjacent laser pulses is between 0.02 µm and 1 µm from center to center of adjacent focal spots, and wherein the focal spots formed by temporally adjacent laser pulses in the pattern overlap; and
    forming an incision with the spaced focal spots in the intrastromal corneal layer of the patient.

2. The method of claim 1 wherein a wavelength of the laser is between 1020 nm and 1065 nm.

3. The method of claim 1 wherein a spot size is between 0.9 µm and 1.11 µm in diameter.

4. The method of claim 1 wherein a frequency of the laser is 10 MHz.

5. The method of claim 1 wherein a pulse width of the laser is between 100 fs and 200 fs.

6. The method of claim 1 wherein an energy for one spot is between 70 nJ and 130 nJ.

7. The method of claim 1 further comprising, continuously scanning the laser beam to produce a scan line, wherein a frequency of the scanning is between 2,000 Hz to 20,000 Hz.

8. The method of claim 1, wherein the wavelength of the laser is between 1020 nm and 1065 nm, the pulse frequency of the laser is 10 MHz, the pulse width of the laser is between 100 fs and 200 fs, the pulse energy of the laser is between 70 nJ and 130 nJ, and the spot size is between 0.9 μm and 1.11 μm in diameter.

9. A system for delivering laser treatment into a cornea of an eye, the system comprising:
- a laser system configured to generate a pulsed femtosecond laser beam;
- a resonant scanner configured to continuously scan the pulsed laser beam to produce a scan line;
- an XY-scan device configured to move the pulsed laser beam in two direction perpendicular to an optical axis of the laser system;
- a Z-scan device configured to modify a depth of a focus of the pulsed laser beam along the optical axis; and
- an optical system configured to focus the pulsed laser beam into a focal spot in the cornea of the eye;
- a controller configured to control the resonant scanner, the XY-scan device and the Z-scan device to create a pattern of spaced overlapping focal spots that each have a diameter between 0.9 μm and 1.11 μm, wherein focal spots formed by temporally adjacent laser pulses overlap each other, wherein the pattern of spaced overlapping spots disrupt cells in the cornea to form an incision within the cornea.

10. The system of claim 9, wherein a wavelength of the laser is between 300 nm and 1100 nm, a pulse frequency of the laser is between 1 and 20 MHz, a pulse width of the laser is between 50 fs and 200 fs, a pulse energy of the laser is between 20 nJ and 200 nJ, and wherein a spot spacing is between 0.02 μm and 1 μm from center to center of adjacent focal spots.

11. The system of claim 10, wherein a wavelength of the laser is between 1020 nm and 1065 nm, a pulse frequency of the laser is 10 MHz, a pulse width of the laser is between 100 fs and 200 fs, and a pulse energy of the laser is between 70 nJ and 130 nJ.

* * * * *